US012751941B2

(12) United States Patent
Qian et al.

(10) Patent No.: US 12,751,941 B2
(45) Date of Patent: Oct. 6, 2026

(54) STABLE PHARMACEUTICAL COMPOSITIONS OF EDARAVONE AND DEXTROCAMPHOL

(71) Applicants: SIMCERE PHARMACEUTICAL CO., LTD., Nanjing (CN); JIANGSU SIMCERE PHARMACEUTICAL CO., LTD., Nanjing (CN)

(72) Inventors: Yong Qian, Nanjing (CN); Xia Wang, Nanjing (CN); Xi Zhu, Nanjing (CN); Cuncun Liu, Nanjing (CN); Feng Wang, Nanjing (CN); Jinsheng Ren, Nanjing (CN)

(73) Assignees: SIMCERE PHARMACEUTICAL CO., LTD., Nanjing (CN); JIANGSU SIMCERE PHARMACEUTICAL CO., LTD., Nanjing (CN)

( * ) Notice: Subject to any disclaimer, the term of this patent is extended or adjusted under 35 U.S.C. 154(b) by 787 days.

(21) Appl. No.: 18/041,764

(22) PCT Filed: Aug. 16, 2021

(86) PCT No.: PCT/CN2021/112813

§ 371 (c)(1),
(2) Date: Feb. 15, 2023

(87) PCT Pub. No.: WO2022/037537

PCT Pub. Date: Feb. 24, 2022

(65) Prior Publication Data

US 2023/0364059 A1 Nov. 16, 2023

(30) Foreign Application Priority Data

Aug. 17, 2020 (CN) ........................ 202010827343.0

(51) Int. Cl.

| | |
|---|---|
| *A61K 31/4152* | (2006.01) |
| *A61K 31/045* | (2006.01) |
| *A61K 47/02* | (2006.01) |
| *C07D 231/24* | (2006.01) |

(52) U.S. Cl.

CPC ........ *A61K 31/4152* (2013.01); *A61K 31/045* (2013.01); *A61K 47/02* (2013.01); *C07D 231/24* (2013.01)

(58) Field of Classification Search

CPC .............. A61K 2300/00; A61K 31/045; A61K 31/4152; A61K 47/02; A61K 9/08; A61P 21/00; A61P 9/10; C07D 231/24

See application file for complete search history.

(56) References Cited

FOREIGN PATENT DOCUMENTS

| | | | |
|---|---|---|---|
| CN | 101721408 | A | 6/2010 |
| CN | 101805292 | A | 8/2010 |
| CN | 101933899 | A | 1/2011 |
| CN | 106668004 | A | 5/2017 |

(Continued)

OTHER PUBLICATIONS

CN111346089 English translation (Year: 2019).*

(Continued)

*Primary Examiner* — Savitha M Rao

(74) *Attorney, Agent, or Firm* — NKL Law; Allen Xue

(57) ABSTRACT

A stable pharmaceutical composition contains active ingredients of edaravone and dextrocamphol can control the content of unique impurity SCR-756 and impurity SCR-757 thereof.

10 Claims, 6 Drawing Sheets

(56) References Cited

FOREIGN PATENT DOCUMENTS

| | | | | | |
|---|---|---|---|---|---|
| CN | 106727287 | A | | 5/2017 | |
| CN | 111346089 | A | | 6/2020 | |
| CN | 111346090 | A | | 6/2020 | |
| WO | 2016197945 | A1 | | 12/2016 | |
| WO | WO-2021229466 | A1 | * | 11/2021 | ......... A61K 31/4152 |

OTHER PUBLICATIONS

Dexborneol data sheet (Year: 2025).*
CN 111346090 English translation (Year: 2018).*
CN 106727287 English translation (Year: 2017).*
Lin, Guanxiong et al.; "Study of the formulation and process of Edaravone injection" ; Strait Pharmaceutical Journal; vol. 17, No. 5; Dec. 31, 2015; pp. 17-20.
Wang, Shengli et al.; "Synthesis of the Related Substances of Edaravone"; Chinese Journal of Pharmaceuticals; vol. 49, No. 5; Dec. 31, 2018; pp. 595-599.
"Annotations to the Pharmacopoeia of the People's Republic of China, Part II", edited by the National Pharmacopoeia Commission, China Medical Science and Technology Press, Aug. 31, 2018, pp. 1769-1770.

* cited by examiner

STABLE PHARMACEUTICAL COMPOSITIONS OF EDARAVONE AND DEXTROCAMPHOL

CROSS-REFERENCE TO RELATED APPLICATIONS

This application is a U.S. national stage entry of PCT international application no. PCT/CN2021/112813, filed on Aug. 16, 2021, which claims the right of priority to the prior application with the patent application number of CN 202010827343.0, entitled "Stable Pharmaceutical Composition," and was submitted to the China National Intellectual Property Administration on Aug. 17, 2020, the content of each is incorporated herein by reference in its entirety.

TECHNICAL FIELD

The present invention belongs to the technical field of medicine, and relates to a stable pharmaceutical composition, in particular to a pharmaceutical composition having active ingredients of edaravone (3-methyl-1-phenyl-2-pyrazolin-5-one) and dextrocamphol.

BACKGROUND ART

In the past 15 years, cerebral stroke has been a cause of death as well as serious and long-term neurological diseases, ranking second worldwide and first in China. The epidemiological situation of acute cerebral stroke treatment status in China was investigated in CHINA QUEST (Quality Evaluation of Stroke Care and Treatment) study. The study suggests that ischemic stroke patients in China presented to the hospital within 20.1 hours on average from the onset of the disease; a considerable number of patients presented to the hospital after 24 hours and these patients have not been effectively treated with drugs. It is clearly explained in the instructions (usage and dosage part) of edaravone injection, which is widely used for treating acute ischemic stroke clinically, that dosing starts within 24 hours after the onset of the disease.

Furthermore, drug quality control has gradually become the focus and challenge in drug development.

Therefore, a technical problem urgently to be solved in the art is to provide a pharmaceutical composition of edaravone that has a long treatment time window, a significant treatment effect, a good stability, and a high medication safety.

SUMMARY OF THE INVENTION

The present invention provides a pharmaceutical composition comprising edaravone, dextrocamphol, sodium metabisulfite and a solvent, wherein the content of sodium metabisulfite is 0.95-1.05 mg/ml.

In some embodiments, the pharmaceutical composition comprises edaravone, dextrocamphol, sodium metabisulfite, a co-solvent and a solvent, wherein the content of sodium metabisulfite is 0.95-1.05 mg/ml.

In some embodiments, the content of sodium metabisulfite is 0.95-1.05 mg/ml, for example, 0.97-1.03 mg/ml, exemplarily 0.95 mg/ml, 0.96 mg/ml, 0.97 mg/ml, 0.98 mg/ml, 0.99 mg/ml, 1.0 mg/ml, 1.01 mg/ml, 1.02 mg/ml, 1.03 mg/ml, 1.04 mg/ml, and 1.05 mg/ml. In some embodiments, the content of sodium metabisulfite is 1.0 mg/ml.

In some embodiments, the weight ratio of edaravone to dextrocamphol in the pharmaceutical composition is 1:1-4:1, for example, 2:1, 2.5:1, 3:1, or 3.5:1.

In some embodiments, the weight ratio of edaravone to dextrocamphol in the pharmaceutical composition is 4:1.

In some embodiments, the weight ratio of edaravone, dextrocamphol, and sodium metabisulfite in the pharmaceutical composition is 4:1:2.

According to the technical solution of the present invention, the content of edaravone in the pharmaceutical composition is 1.0-3.0 mg/ml, for example, 1.5-2.5 mg/ml. In some embodiments, the content of edaravone in the pharmaceutical composition is 2.0 mg/ml.

According to the technical solution of the present invention, the content of dextrocamphol in the pharmaceutical composition is 0.2-1.0 mg/ml, for example, 0.3-0.8 mg/ml. In some embodiments, the content of dextrocamphol in the pharmaceutical composition is 0.5 mg/ml.

In some embodiments, the content of edaravone, dextrocamphol, and sodium metabisulfite in the pharmaceutical composition is 2.0 mg/ml, 0.5 mg/ml, and 1.0 mg/ml, respectively.

In some embodiments, the co-solvent is selected from propylene glycol, ethanol, or tert-butanol.

In some embodiments, the solvent is selected from water for injection.

In some embodiments, the co-solvent and the solvent are propylene glycol and water for injection, respectively.

According to the technical solution of the present invention, the content of the co-solvent in the pharmaceutical composition is 0.01-0.15 ml/ml, for example, 0.03-0.12 ml/ml, exemplarily 0.05 ml/ml, 0.08 ml/ml, and 0.1 ml/ml.

In some embodiments, the content of edaravone, dextrocamphol, sodium metabisulfite, and propylene glycol in the pharmaceutical composition is 2.0 mg/ml, 0.5 mg/ml, 1.0 mg/ml, and 0.08 ml/ml, respectively.

In some embodiments, the content of edaravone, dextrocamphol, sodium metabisulfite, and propylene glycol in the pharmaceutical composition is respectively 2.0 mg/ml, 0.5 mg/ml, 1.0 mg/ml, and 0.08 ml/ml, and the balance is water for injection.

According to an exemplary embodiment of the present invention, the dose (single dose) of the pharmaceutical composition as a solution is 5 ml and contains 10 mg of edaravone, 2.5 mg of dextrocamphol, 5 mg of sodium metabisulfite, and 0.4 ml of propylene glycol, with the rest being water for injection.

According to the technical solution of the present invention, the active ingredients of the pharmaceutical composition are edaravone and dextrocamphol.

According to the technical solution of the present invention, the pharmaceutical composition may also contain a compound of formula I or a pharmaceutically acceptable salt thereof, Formula I

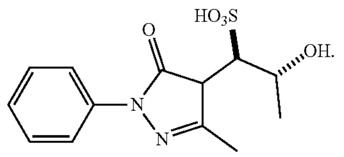

Further, the weight ratio of the compound of formula I or a pharmaceutically acceptable salt thereof to edaravone is 0.3% or less, for example, 0.29% or less, 0.28% or less, 0.27% or less, 0.26% or less, 0.25% or less, 0.2% or less, 0.15% or less, and 0.1% or less.

According to the technical solution of the present invention, the pharmaceutical composition may also contain a compound of formula II or a pharmaceutically acceptable salt thereof, Formula II

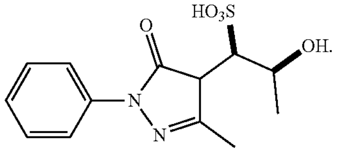

Further, the weight ratio of the compound of formula II or a pharmaceutically acceptable salt thereof to edaravone is 0.3% or less, for example, 0.29% or less, 0.28% or less, 0.27% or less, 0.26% or less, 0.25% or less, 0.2% or less, 0.15% or less, and 0.1% or less.

In another aspect, the present invention provides a pharmaceutical composition, wherein the pharmaceutical composition comprises edaravone, dextrocamphol, sodium metabisulfite, a co-solvent, and a solvent, the content of sodium metabisulfite is 0.95-1.05 mg/ml, and the pharmaceutical composition also contains the compound of formula I or a pharmaceutically acceptable salt thereof at a weight ratio to edaravone of 0.3% or less, Formula I

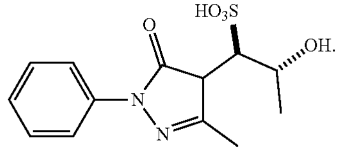

In another aspect, the present invention provides a pharmaceutical composition, wherein the pharmaceutical composition comprises edaravone, dextrocamphol, sodium metabisulfite, a co-solvent, and a solvent, the content of sodium metabisulfite is 0.95-1.05 mg/ml, and the pharmaceutical composition also contains the compound of formula II or a pharmaceutically acceptable salt thereof at a weight ratio to edaravone of 0.3% or less, Formula II

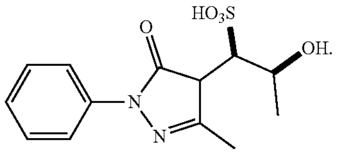

In another aspect, the present invention provides a pharmaceutical composition, wherein the pharmaceutical composition comprises edaravone, dextrocamphol, sodium metabisulfite, a co-solvent, and a solvent, the content of sodium metabisulfite is 0.95-1.05 mg/ml, and the pharmaceutical composition also comprises the compound of formula I or a pharmaceutically acceptable salt thereof at a weight ratio to edaravone of 0.3% or less and the compound of formula II or a pharmaceutically acceptable salt thereof at a weight ratio to edaravone of 0.3%.

The present invention also provides a compound as represented by formula I or a pharmaceutically acceptable salt thereof, Formula I

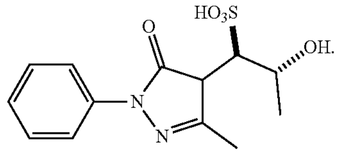

The present invention also provides a compound as represented by formula II or a pharmaceutically acceptable salt thereof, Formula II

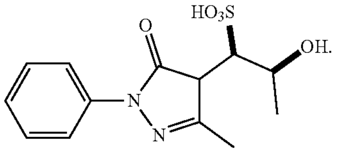

According to the technical solution of the present invention, the pharmaceutically acceptable salt is an alkali metal salt, such as a potassium salt, a sodium salt or a lithium salt.

The present invention also provides the use of the above-mentioned pharmaceutical composition in the preparation of a pharmaceutical preparation for treating cerebral stroke.

The present invention also provides the use of the above-mentioned pharmaceutical composition in the treatment of cerebral stroke.

The present invention also provides the above-mentioned pharmaceutical composition for treating cerebral stroke.

The present invention also provides the use of the above-mentioned pharmaceutical composition in the preparation of a drug for treating amyotrophic lateral sclerosis or related disorders.

The present invention also provides the use of the above-mentioned pharmaceutical composition in the treatment of amyotrophic lateral sclerosis or related disorders.

The present invention also provides the above-mentioned pharmaceutical composition for treating amyotrophic lateral sclerosis or related disorders.

The present invention also provides a method for preventing and/or treating cerebral stroke, which method comprises administering a therapeutically effective amount of the pharmaceutical composition or pharmaceutical preparation to a subject to be treated, such as a human.

The present invention also provides a method for preventing and/or treating amyotrophic lateral sclerosis or related disorders, which method comprises administering a therapeutically effective amount of the pharmaceutical composition or pharmaceutical preparation to a subject to be treated, such as a human.

The present invention also provides the use of the compound as represented by formula I or a pharmaceutically acceptable salt thereof mentioned above in the quality control of the pharmaceutical composition or pharmaceutical preparation.

The present invention also provides the use of the compound as represented by formula II or a pharmaceutically acceptable salt thereof acceptable salt thereof mentioned above in the quality control of the pharmaceutical composition or pharmaceutical preparation.

The present invention also provides a method for preparing the compound of formula I or a tautomer thereof, characterized in that the method comprises subjecting intermediate 2 to a reduction reaction to obtain the compound of formula I or a tautomer thereof,

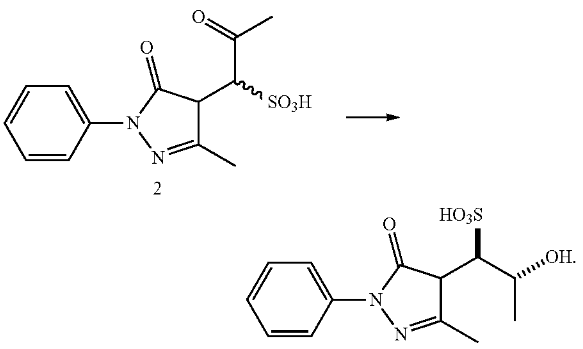

2

The present invention also provides a method for preparing the compound of formula II or a tautomer thereof, characterized in that the method comprises subjecting intermediate 2 to a reduction reaction to obtain the compound of formula II or a tautomer thereof,

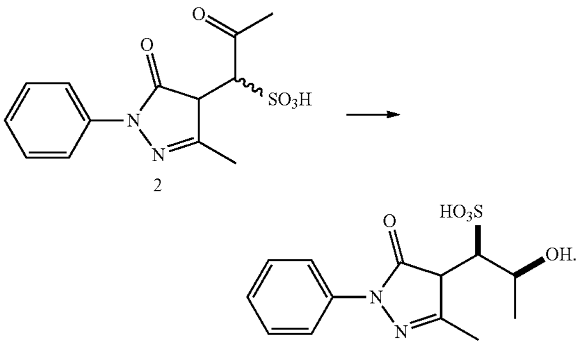

2

According to the technical solution of the present invention, intermediate 2 is subjected to a reaction in the presence of a reducing agent and a solvent to obtain the compound of formula I or a tautomer thereof.

According to the technical solution of the present invention, intermediate 2 is subjected to a reaction in the presence of a reducing agent and a solvent to obtain the compound of formula II or a tautomer thereof.

In some embodiments, the reducing agent is selected from sodium borohydride, potassium borohydride, lithium borohydride, zinc borohydride, sodium cyanoborohydride, sodium triacetoxyborohydride, and/or lithium cyanoborohydride.

In some embodiments, the reducing agent is selected from sodium borohydride.

In some embodiments, the solvent is selected from protic solvents.

In some embodiments, the solvent is selected from one or more of water, methanol, ethanol, propanol, and isopropanol.

In some embodiments, the solvent is selected from methanol.

The present invention also provides a method for preparing intermediate 2, characterized in that the method comprises reacting intermediate 1 with a sulfonating agent to obtain intermediate 2,

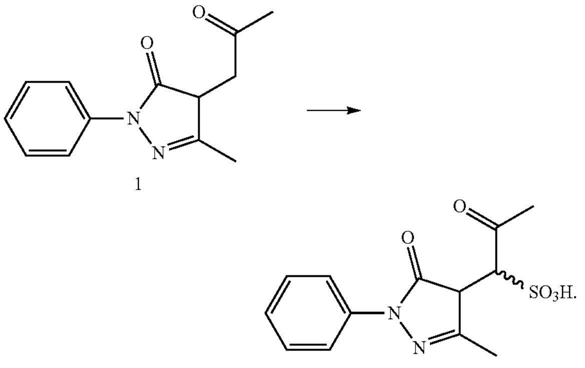

1

2

In some embodiments, the sulfonating agent is sulfur trioxide and/or an adduct of sulfur trioxide.

In some embodiments, the sulfonating agent is a sulfur trioxide-dioxane adduct.

In some embodiments, intermediate 1 can be prepared by the reaction below

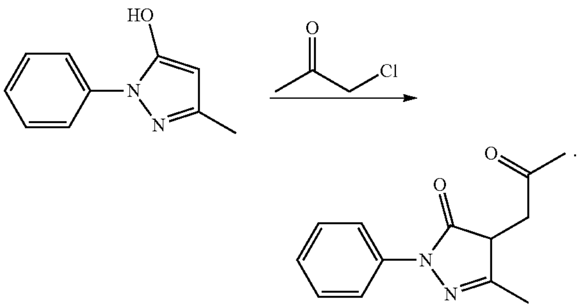

Beneficial Effects of the Present Invention

The inventors found during drug development that the pharmaceutical compositions containing the active ingredients of edaravone and dextrocamphol are prone to two impurities that have novel structures: impurity SCR-756 and impurity SCR-757. Once produced, the impurities SCR-756 and SCR-757 would be at a content which generally exceeds the detection threshold of 0.1%, and the content of the two is difficult to be controlled within a reasonable range. Furthermore, stability tests have shown that the content of impurity SCR-756, impurity SCR-757 and the total impurities of edaravone would increase at an elevated rate with the rise of the storage temperature and the extension of the storage period. In addition, the above-mentioned problems cannot be effectively solved by the conventional methods of controlling the temperature, pH value, co-solvent, preparation time and other factors in the process steps. However, the inventors unexpectedly found from a great number of experiments that the amount of sodium metabisulfite greatly affects the content of impurity SCR-756, impurity SCR-757 and the total impurities in the pharmaceutical composition, and if the amount of sodium metabisulfite is too low or too high, impurity SCR-756, impurity SCR-757 and the total impurities would not be effectively controlled. Therefore, by adding sodium metabisulfite and controlling its amount at a suitable range, the impurities in the composition and the product quality that are difficult to control, the content of the impurities increasing at an elevated rate with the rise of the storage temperature or the extension of the storage period, and other technical problems are effectively solved in the present invention. In particular, the content of impurity SCR-756, impurity SCR-757 and the total impurities of edaravone in the pharmaceutical composition can be unexpectedly controlled, and the problems of impurities and product quality being difficult to control, the storage life being short, medication safety, etc. are solved from the source.

The term “tautomer” herein refers to structural isomers having different energy levels that are interconvertible via a low energy barrier. Where tautomerization is possible (such as in solution), a chemical equilibrium of tautomers can be achieved. For example, proton tautomers (also known as prototropic tautomers) include interconversion via migration of a proton, such as keto-enol isomerization and imine-enamine isomerization. Unless otherwise indicated, all tautomeric forms of the compounds in the present invention are within the scope of the present invention.

A person skilled in the art should be aware that α-H-containing carbonyl compounds exhibit the tautomerism of ketone form-enol form, and the tautomers are interconvertible and generally exist in equilibrium form. Therefore, a person skilled in the art should be aware that the compounds of formula I and formula II in the present invention all exhibit tautomerism and the tautomers are interconvertible. In some embodiments of the present invention, for the convenience of description and expression, the compounds with tautomerism can be represented only by the ketone form (such as compound of formula I or formula II), or only by the enol form (such as compound of formula I' or formula II'). The compounds as represented by formula I or formula II herein comprise both the compounds in ketone form and the corresponding compounds in enol form.

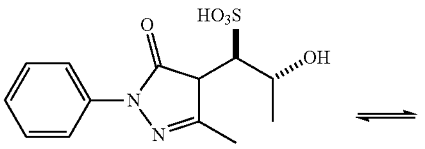

Formula I (ketone form)

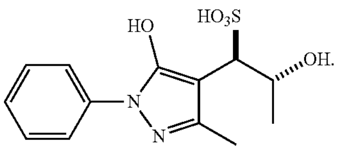

Formula I' (enol form)

DETAILED DESCRIPTION OF EMBODIMENTS

Figure 1:
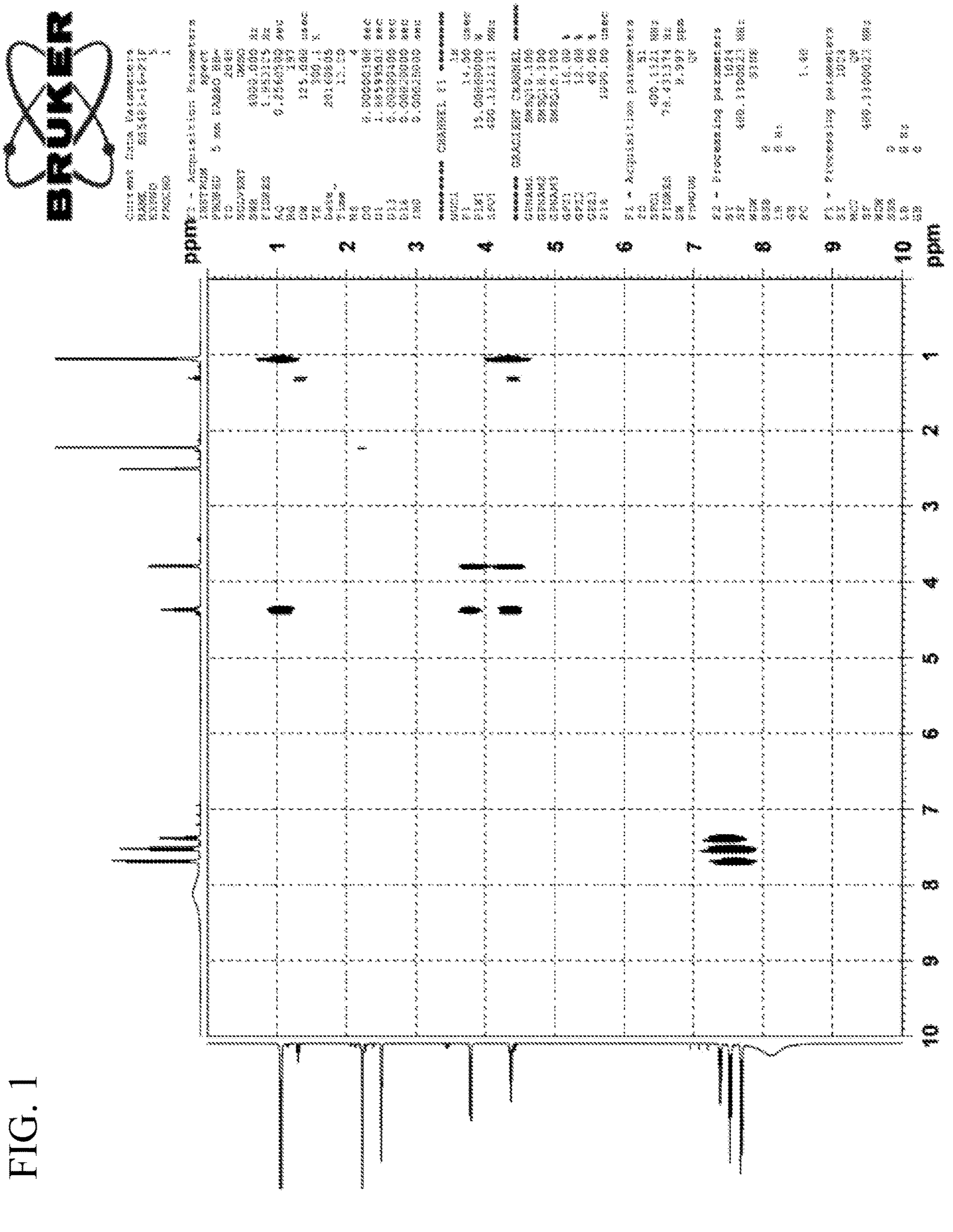
FIG. 1 is the COSY spectrum of SCR-756.

The technical solutions of the present invention will be further described in detail below in conjunction with specific examples. It should be understood that the following examples are only to illustrate and explain the present invention, and should not be understood as limiting the scope of protection of the present invention. All techniques achieved based on the above-mentioned content of the present invention fall within the scope of protection of the present invention.

Unless otherwise stated, the raw materials and reagents used in the following examples are commercially available or can be prepared by known methods.

Example 1

Investigation of Amount of Sodium Metabisulfite and Related Substances

Propylene glycol was heated to 50-60° C., edaravone was added, and the mixture was stirred until complete dissolution to obtain a medicinal solution. The medicinal solution was cooled to 25° C. or less, dextrocamphol (the structure being

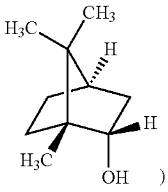

)

was added, and the mixture was stirred until complete dissolution. Sodium metabisulfite was added to an appropriate amount of water (25° C. or less) and the mixture was stirred until dissolution. The sodium metabisulfite solution was slowly added to the medicinal solution with stirring, and then water was slowly added to make the amount close to the formulation amount. The pH was adjusted to 4.5±0.2 with 0.1 mol/L of hydrochloric acid and sodium hydroxide solution, water was added to achieve the formulation amount, and the resulting medicinal solution was filtered, sealed after nitrogen filling, and sterilized.

According to the above-mentioned method, pharmaceutical compositions having a sodium metabisulfite content of 0.5 mg/mL, 0.8 mg/mL, 1.0 mg/mL, 1.2 mg/mL, and 1.5 mg/mL were prepared and obtained, and the specific formulations thereof are as shown in Table 1.

TABLE 1

| Formulation information of pharmaceutical compositions F1-F5 | | | | | |
|---|---|---|---|---|---|
| Formulation components | F1 | F2 | F3 | F4 | F5 |
| Edaravone | 10 mg | 10 mg | 10 mg | 10 mg | 10 mg |
| Dextrocamphol | 2.5 mg | 2.5 mg | 2.5 mg | 2.5 mg | 2.5 mg |
| Propylene glycol (for injection) | 0.4 mL | 0.4 mL | 0.4 mL | 0.4 mL | 0.4 mL |
| Sodium metabisulfite | 2.5 mg | 4 mg | 5 mg | 6 mg | 7.5 mg |
| hydrochloric acid | q.s. | q.s. | q.s. | q.s. | q.s. |
| Sodium hydroxide | q.s. | q.s. | q.s. | q.s. | q.s. |
| Water for injection | Making up to 5 mL | Making up to 5 mL | Making up to 5 mL | Making up to 5 mL | Making up to 5 mL |

The related substances in the pharmaceutical compositions in Table 1 were analyzed. The samples were placed at the temperature of 60° C., and the content of impurity SCR-756, impurity SCR-757 and the total impurities of edaravone in the samples was determined at 0 days and 10 days, respectively. The specific results are as shown in Table 2.

TABLE 2

| Investigation results of content[1] of impurity SCR-756, impurity SCR-757 and total impurities | | | |
|---|---|---|---|
| Sample batch number | Impurity | 60° C., 0 days (%) | 60° C., 10 days (%) |
| F1 | SCR-756 | 0.12 | 0.39 |
| | SCR-757 | 0.09 | 0.32 |
| | Total impurities | 0.48 | 2.13 |
| F2 | SCR-756 | 0.18 | 0.47 |
| | SCR-757 | 0.15 | 0.40 |
| | Total impurities | 0.66 | 2.25 |
| F3 | SCR-756 | 0.16 | 0.29 |
| | SCR-757 | 0.13 | 0.25 |
| | Total impurities | 0.57 | 1.55 |
| F4 | SCR-756 | 0.19 | 0.39 |
| | SCR-757 | 0.16 | 0.34 |
| | Total impurities | 0.64 | 1.85 |
| F5 | SCR-756 | 0.23 | 0.38 |
| | SCR-757 | 0.20 | 0.33 |
| | Total impurities | 0.77 | 1.78 |

Notes: [1] "Content" refers to the weight ratio of impurity SCR-756, impurity SCR-757 and the total impurities to edaravone in the pharmaceutical composition.

Analysis method of the related substances: an appropriate amount of the sample was taken and diluted by adding a solvent, i.e., methanol-water (volume ratio: 32:68) to prepare an edaravone solution (about 0.5 mg/mL) as a test solution. An appropriate amount was accurately measured and an edaravone solution (5 μg/mL) was prepared as a control solution by dilution with the solvent. Impurity control SCR-756 and SCR-757 (5 mg each) were accurately weighed and placed in a 100 mL volumetric flask. A solvent was added, and the mixture was sonicated to aid dissolution, diluted to scale, and shaken uniformly to obtain an impurity stock solution. In addition, 10 mg of edaravone control was weighed accurately, placed in a 20 mL volumetric flask, and dissolved by adding 5 mL of methanol. 1 mL of the impurity stock solution was added, and the mixture was diluted to scale by adding a solvent, and shaken uniformly to obtain a system suitability solution. The determination was performed according to the high performance liquid chromatography (General rule 0512, Volume IV, Pharmacopoeia of the People's Republic of China (2015)). Octadecyl silane bonded silica gel was used as the filler (Agilent Eclipse plus C18 4.6×150 mm, 3.5 μm), 0.5% triethylamine (pH 6.3, adjusted with phosphoric acid) was used as mobile phase A, and methanol was used as mobile phase B. Elution with a linear gradient was performed according to the table below. The detection wavelength was 248 nm. 10 μL of the system suitability solution was accurately measured and injected into the liquid chromatograph, and the chromatogram was recorded. The peaks of impurity SCR-756, impurity SCR-757 and edaravone appeared in sequence, and the retention time of edaravone peak was about 6 minutes. The test solution and the control solution (10 μL each) were accurately measured and separately injected into the liquid chromatograph and the chromatograms were record.

| Time (min) | Mobile phase A (%) | Mobile phase B (%) |
|---|---|---|
| 0 | 68 | 32 |
| 8 | 68 | 32 |
| 15 | 40 | 60 |
| 30 | 40 | 60 |
| 31 | 68 | 32 |

Example 2

Propylene glycol was heated to 50-60° C., edaravone was added, and the mixture was stirred until complete dissolution to obtain a medicinal solution. The medicinal solution was cooled to 25° C. or less, dextrocamphol was added, and the mixture was stirred until complete dissolution. An antioxidant (one or two of sodium metabisulfite, sodium bisulfite, or L-cysteine hydrochloride) was added to an appropriate amount of water at 25° C. or less, and the mixture was stirred until dissolution. The above-mentioned antioxidant solution was slowly added to the medicinal solution with stirring, and then water was slowly added to make the amount close to the formulation amount. The pH was adjusted to 4.5±0.2 with 0.1 mol/L of hydrochloric acid and sodium hydroxide solution, water was added to achieve the formulation amount (as shown in Table 3), and the resulting medicinal solution was filtered, sealed after nitrogen filling, and sterilized. The appearance of the samples and the impurities of edaravone were mainly investigated, and the results are as shown in Table 4.

TABLE 3

| Based on the amount of 3000 vials | Formulation 1 | Formulation 2 | Formulation 3 |
|---|---|---|---|
| Edaravone (g) | 30 | 30 | 30 |
| Dextrocamphol (g) | 7.5 | 7.5 | 7.5 |

TABLE 3-continued

| Based on the amount of 3000 vials | Formulation 1 | Formulation 2 | Formulation 3 |
|---|---|---|---|
| Sodium metabisulfite (g) | 15 | 15 | — |
| Sodium bisulfite (g) | — | — | 15 |
| L-cysteine hydrochloride (g) | — | 7.5 | 7.5 |
| Propylene glycol (L) | 1.2 | 1.2 | 1.2 |
| Water for injection, making up to (L) | 15 | 15 | 15 |

TABLE 4

| Sample | Formulation number | Appearance | Edaravone-related impurities (%) |
|---|---|---|---|
| Before sterilization | Formulation 1 | Colorless clear liquid | 0.29 |
| | Formulation 2 | Colorless clear liquid | 0.28 |
| | Formulation 3 | Colorless clear liquid | 0.38 |
| After sterilization | Formulation 1 | Colorless clear liquid | 0.42 |
| | Formulation 2 | Colorless clear liquid | 0.49 |
| | Formulation 3 | Colorless clear liquid | 0.53 |
| After sterilization 40° C., 1 month | Formulation 1 | Colorless clear liquid | 0.58 |
| | Formulation 2 | Colorless clear liquid | 0.56 |
| | Formulation 3 | Colorless clear liquid | 0.66 |

The amount of edaravone-related impurities in formulations 1 and 2 was significantly lower than that in formulation 3.

The analysis method of the related substances was as follows:

the determination was performed according to the high performance liquid chromatography (Appendix VI E, Volume II, Pharmacopoeia of the People's Republic of China (2010)). Octadecyl silane bonded silica gel was used as the filler (Waters sunfire C18, 4.6×250 mm, 5.0 μm), 0.02 mol/L of ammonium acetate solution (pH 4.0, adjusted with glacial acetic acid) was used as mobile phase A, and acetonitrile was used as mobile phase B. Elution with a linear gradient was performed according to the table below.

Detection wavelength: 254 nm;

Flow rate: 1.0 ml/min;

Injection volume: 20 μl;

Solvent: 0.02 mol/L of ammonium acetate solution (pH 4.0, adjusted with glacial acetic acid)-acetonitrile (volume ratio: 80:20);

Test solution: 5 ml of the sample was taken, placed in a 20 ml volumetric flask, and diluted to scale by adding the solvent to obtain the test solution;

Control solution: 1 ml of the test solution was accurately measured, placed in a 200 ml volumetric flask, and diluted to scale by adding the solvent to obtain the control solution.

| Time (min) | Mobile phase A (%) | Mobile phase B (%) |
|---|---|---|
| 0 | 80 | 20 |
| 30 | 80 | 20 |
| 40 | 40 | 60 |
| 60 | 40 | 60 |
| 61 | 80 | 20 |

Example 3

Preparation of Compounds SCR-756 and SCR-757

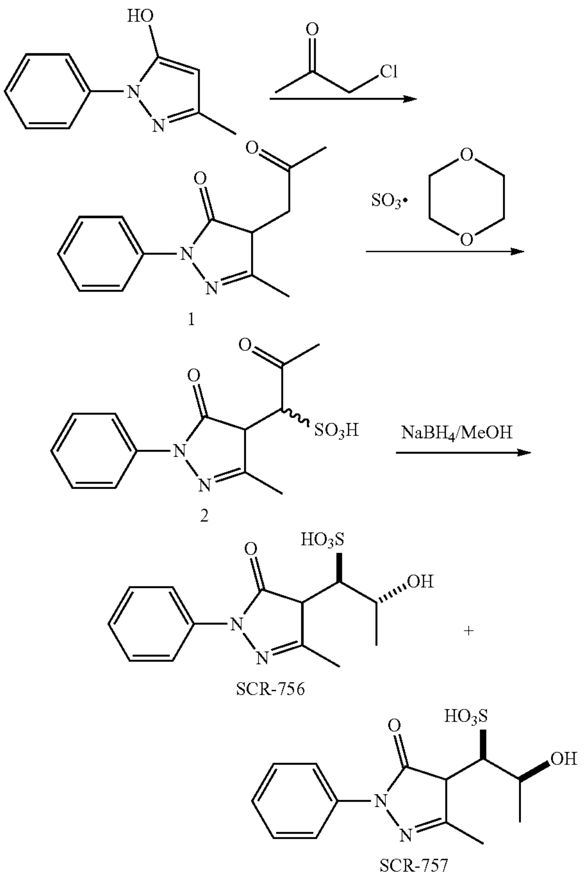

1

2

SCR-756

+

SCR-757

Synthesis Steps:

(1) Preparation of Intermediate 1

Na (39.92 g) was added to 1.25 L of anhydrous ethanol in batches while the temperature was kept constant at 25° C.-40° C., and the mixture was stirred at 50° C. until Na was completely dissolved and the solution was clarified. Edaravone (250 g, solid) was added in batches at 0° C.-5° C. in a dark place away from light, and the mixture was stirred to obtain a turbid liquid. The system was protected with $N_2$ balloon and protected from light with a black plastic bag. Chloroacetone (203.11 g) was dissolved in 750 mL of anhydrous ethanol to prepare an ethanol solution, and the solution was directly added to a dropping funnel. The above-mentioned ethanol solution was added dropwise at −5° C.-0° C. while the system was protected with $N_2$ balloon and protected from light with a black plastic bag, and the mixture was stirred at 0° C.-5° C. for 2 h. It was monitored by TLC (petroleum ether:ethyl acetate=1:1) that most of the raw material, i.e., edaravone, was consumed. The reaction solution was poured into 4 L of ice water with stirring. The resulting mixture was filtered, and the filter cake was washed with water (600 mL*3), then slurried with ethyl acetate (200 mL), and filtered to obtain intermediate 1 (37 g in total).

(2) Preparation of Intermediate 2

To a 3 L three-necked flask, 37 g of intermediate 1 was added. Under the protection of $N_2$ balloon, 650 mL of dichloroethane and 325 mL of anhydrous dioxane were added via an addition funnel. The flask was evacuated and the mixture was stirred until complete dissolution. 4A molecular sieves (100 g) and sulfur trioxide-dioxane adduct (69.41 g) were added in batches successively at 0° C.-5° C. with stirring. The mixture was heated to 100° C., reacted for 8 hours, and then cooled to 25° C. After filtration, the filter cake was rinsed twice with anhydrous dichloromethane, and the filter cake and anhydrous dichloromethane (600 mL) were stirred and filtered to remove the large particles of molecular sieves. The filtrate was stirred for 5 minutes, and then filtered. The filter cake was rinsed twice with anhydrous dichloromethane to obtain a crude product, which was slurried with ethanol and then filtered to obtain intermediate 2 as a solid (30 g).

(3) Preparation of Compounds SCR-756 and SCR-757

To a 2 L three-neck flask, intermediate 2 (30 g) was added. Under the protection of $N_2$ balloon, anhydrous MeOH (600 mL) was added via an addition funnel. The flask was evacuated and the mixture was stirred under dry ice bath. The temperature was kept at 0° C.-5° C. NaBH4 (8.85 g) was added in batches. The reaction solution was stirred at 60° C. for 3 h, subjected to rotary evaporation to remove the solvent, and then separated by HPLC (chromatographic column: YMC-Triart Prep C18 250*50 mm*10 μm; mobile phase: [water (0.1% trifluoroacetic acid)-acetonitrile]; acetonitrile: 0%-28.5%, 19 mins) to obtain compound SCR-756 and compound SCR-757.

The structures of compound SCR-756 and compound SCR-757 were confirmed by nuclear magnetic resonance.

Nuclear Magnetic Resonance (NMR) Spectroscopy

Instrument: BRUKER AV-400 nuclear magnetic resonance instrument

Solvent: DMSO-$d_6$

Internal standard: TMS

Temperature: 300 K.

$^1$H NMR data and $^{13}$C NMR data of SCR-756 are as shown in Table 5-1 and Table 5-2.

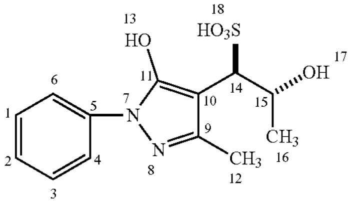

TABLE 5-1

Determination results of $^1$H NMR spectroscopy of SCR-756

| Chemical shift (ppm) | Number of protons | Peak shape | Chemical shifts of related protons (ppm) | Assignment | Notes |
|---|---|---|---|---|---|
| 8.11 | 3H | brs | / | $H_{13}/H_{17}/H_{18}$ | Active hydrogen |
| 7.69 | 2H | d | 7.53, 7.38 | $H_4/H_6$ | J = 8.4 Hz |
| 7.53 | 2H | dd | 7.69, 7.38 | $H_1/H_3$ | $J_1$ = 7.2 Hz, $J_2$ = 8.4 Hz |
| 7.38 | H | dd | 7.69, 7.53 | $H_2$ | $J_1 = J_2$ = 7.2 Hz |
| 4.38 | H | m | 3.79, 1.06 | $H_{15}$ | / |
| 3.79 | H | d | 4.38 | $H_{14}$ | J = 6.0 Hz |

TABLE 5-1-continued

Determination results of $^1$H NMR spectroscopy of SCR-756

| Chemical shift (ppm) | Number of protons | Peak shape | Chemical shifts of related protons (ppm) | Assignment | Notes |
|---|---|---|---|---|---|
| 2.26 | 3H | s | / | $H_{12}$ | / |
| 1.06 | 3H | d | 4.38 | $H_{16}$ | J = 6.0 Hz |

TABLE 5-2

Determination results of $^{13}$C NMR spectroscopy of SCR-756

| Chemical shift (ppm) | Type of carbon | Assignment | Chemical shifts of related protons (ppm) | Chemical shifts of long-range related protons (ppm) |
|---|---|---|---|---|
| 153.1 | Quaternary C | $C_{11}$ | / | 3.79 |
| 148.5 | Quaternary C | $C_9$ | / | 3.79, 2.26 |
| 136.3 | Quaternary C | $C_5$ | / | 7.69, 7.53 |
| 129.7 | Tertiary C | $C_1$, $C_3$ | 7.53 | 7.69, 7.38 |
| 127.7 | Tertiary C | $C_2$ | 7.38 | 7.69 |
| 122.7 | Tertiary C | $C_4$, $C_6$ | 7.69 | 7.69 |
| 96.1 | Quaternary C | $C_{10}$ | / | 4.38, 3.79, 2.26 |
| 67.4 | Tertiary C | $C_{15}$ | 4.38 | 3.79, 1.06 |
| 63.5 | Tertiary C | $C_{14}$ | 3.79 | 4.38, 1.06 |
| 19.9 | Primary C | $C_{16}$ | 1.06 | 4.38, 3.79 |
| 12.4 | Primary C | $C_{12}$ | 2.26 | / |

$^1$H NMR data and $^{13}$C NMR data of SCR-757 are as shown in Table 6-1 and Table 6-2.

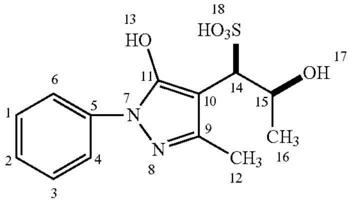

TABLE 6-1

Determination results of $^1$H NMR spectroscopy of SCR-757

| Chemical shift (ppm) | Number of protons | Peak shape | Chemical shifts of related protons (ppm) | Assignment | Notes |
|---|---|---|---|---|---|
| 7.87 | 3H | brs | / | $H_{13}/H_{17}/H_{18}$ | Active hydrogen |
| 7.68 | 2H | d | 7.56, 7.42 | $H_4/H_6$ | J = 8.4 Hz |
| 7.56 | 2H | dd | 7.68, 7.42 | $H_1/H_3$ | $J_1$ = 7.2 Hz, $J_2$ = 8.4 Hz |
| 7.42 | H | dd | 7.68, 7.56 | $H_2$ | $J_1 = J_2$ = 7.2 Hz |
| 4.86 | H | m | 3.70, 1.15 | $H_{15}$ | / |
| 3.70 | H | d | 4.86 | $H_{14}$ | J = 3.2 Hz |
| 2.26 | 3H | s | / | $H_{12}$ | / |
| 1.15 | 3H | d | 4.86 | $H_{16}$ | J = 6.4 Hz |

TABLE 6-2

Determination results of $^{13}C$ NMR spectroscopy of SCR-757

| Chemical shift (ppm) | Type of carbon | Assign-ment | Chemical shifts of related protons (ppm) | Chemical shifts of long-range related protons (ppm) |
|---|---|---|---|---|
| 154.0 | Quaternary C | $C_{11}$ | / | 3.70 |
| 148.7 | Quaternary C | $C_9$ | / | 3.70, 2.26 |
| 135.7 | Quaternary C | $C_5$ | / | 7.68, 7.56 |
| 129.9 | Tertiary C | $C_1$, $C_3$ | 7.56 | 7.68, 7.42 |
| 128.1 | Tertiary C | $C_2$ | 7.42 | 7.68 |
| 122.9 | Tertiary C | $C_4$, $C_6$ | 7.68 | 7.42 |
| 96.9 | Quaternary C | $C_{10}$ | / | 4.86, 3.70, 2.26 |
| 67.4 | Tertiary C | $C_{15}$ | 4.86 | 3.70, 1.15 |
| 62.3 | Tertiary C | $C_{14}$ | 3.70 | 4.86, 1.15 |
| 22.0 | Primary C | $C_{16}$ | 1.15 | 3.70 |
| 11.9 | Primary C | $C_{12}$ | 2.26 | / |

Figure 2:
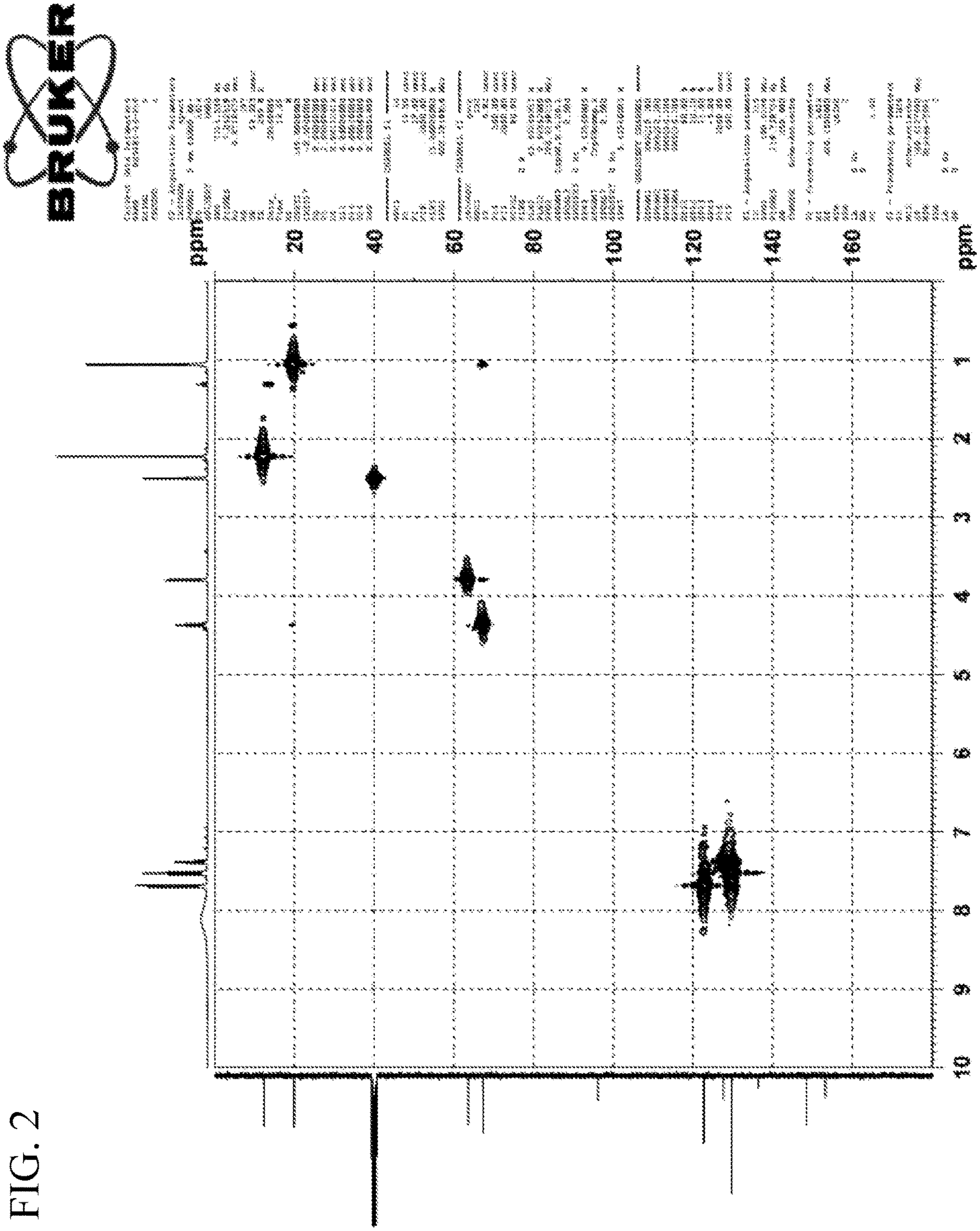
FIG. 2 is the HSQC spectrum of SCR-756.
Figure 3:
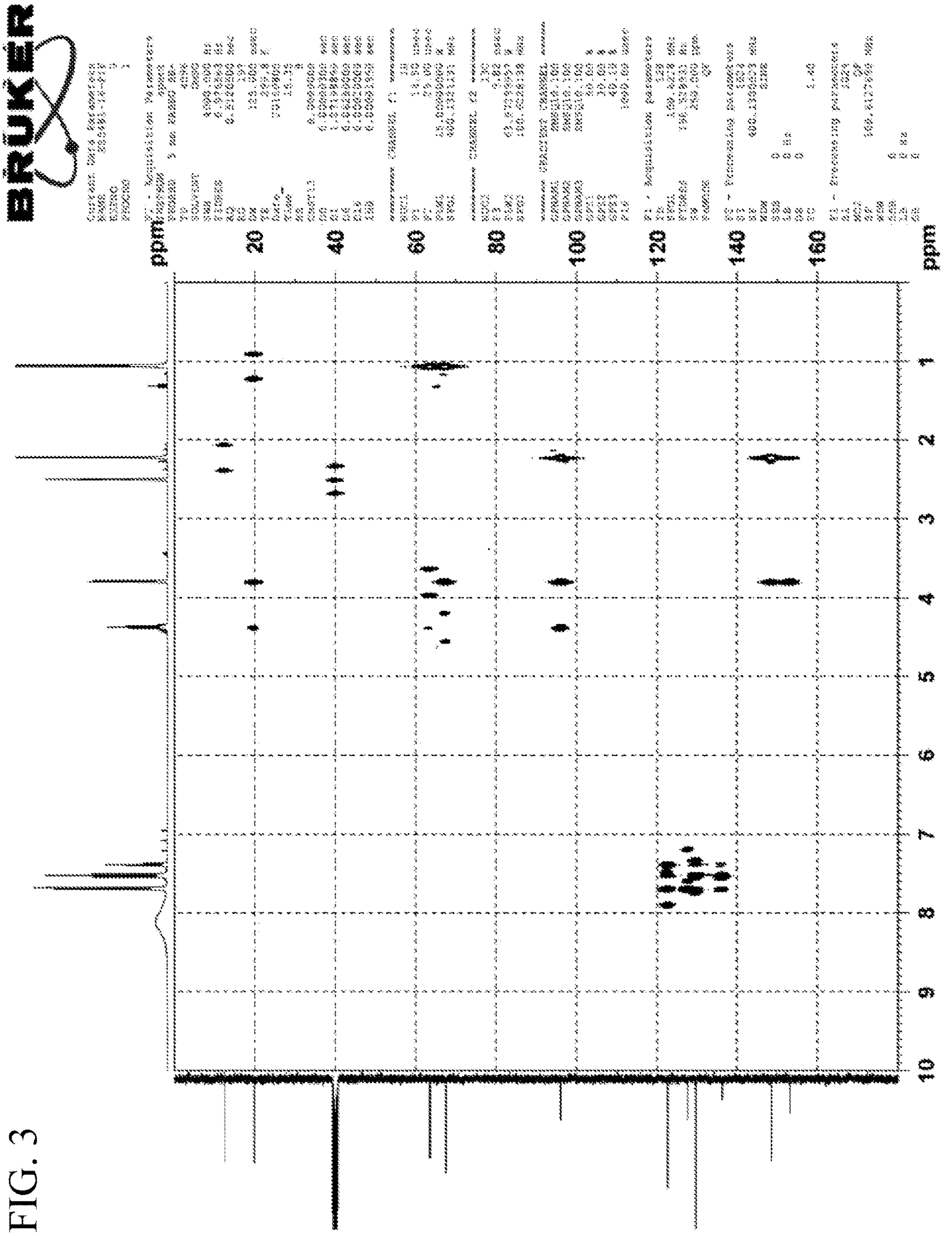
FIG. 3 is the HMBC spectrum of SCR-756.
Figure 4:
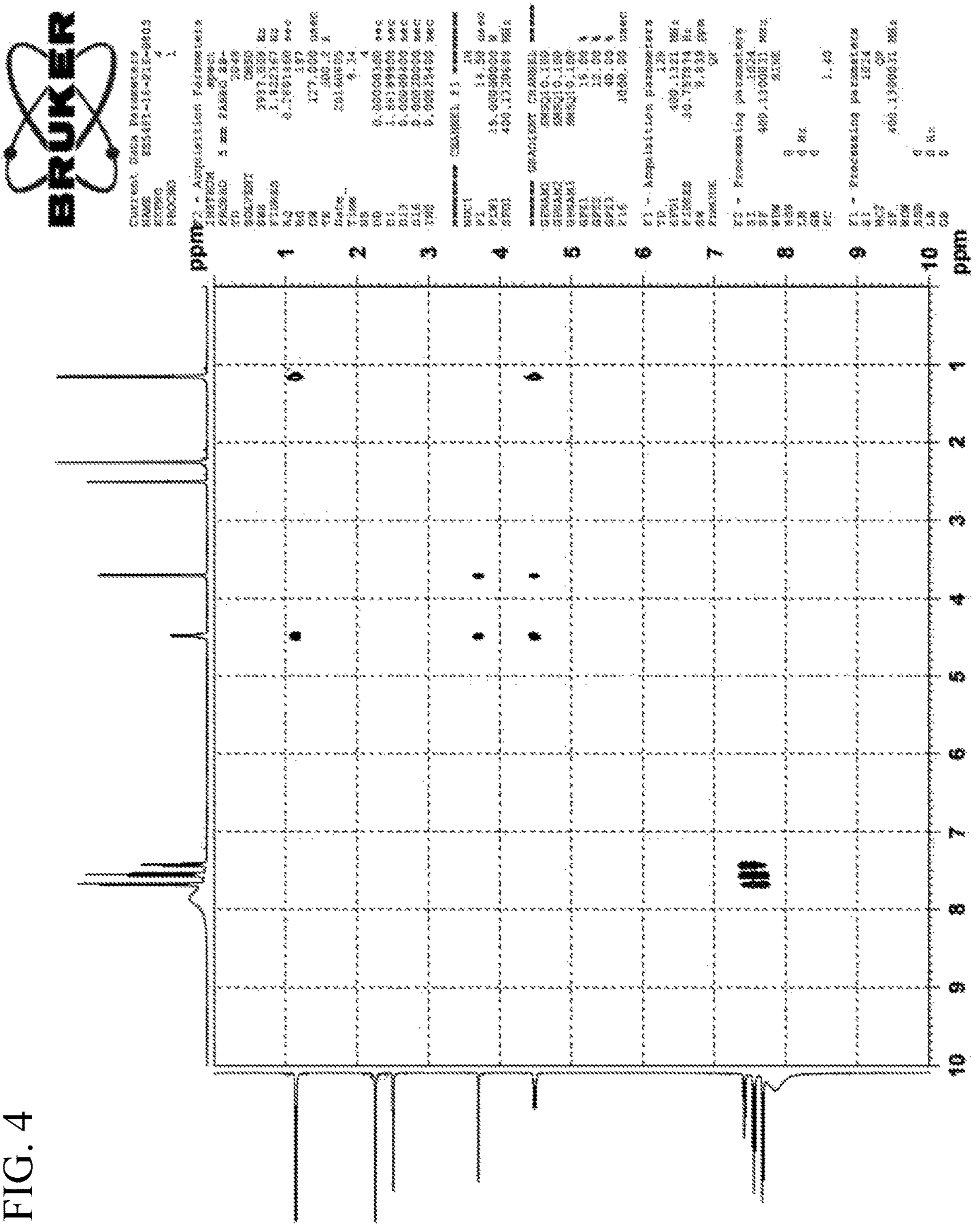
FIG. 4 is the COSY spectrum of SCR-757.
Figure 5:
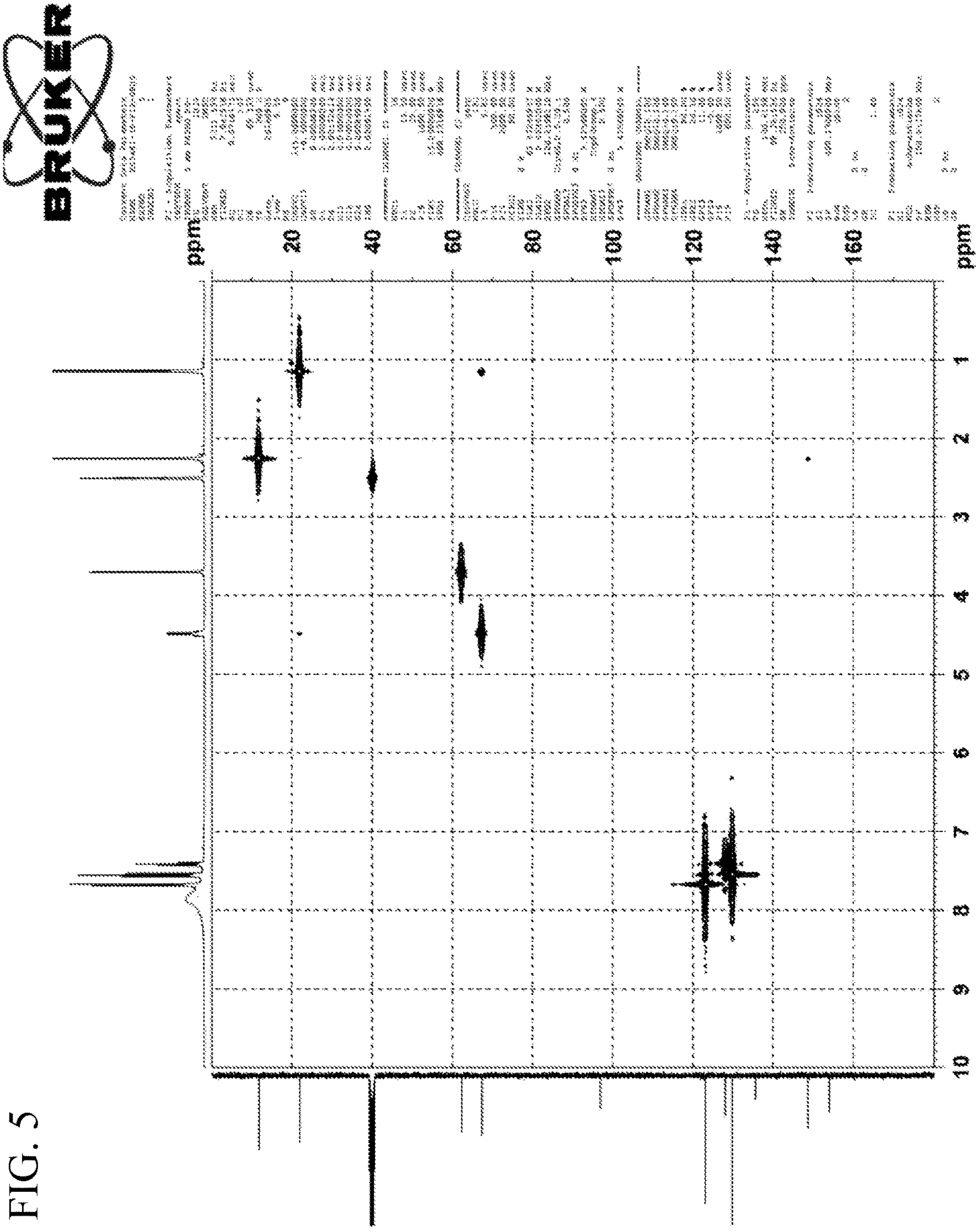
FIG. 5 is the HSQC spectrum of SCR-757.
Figure 6:
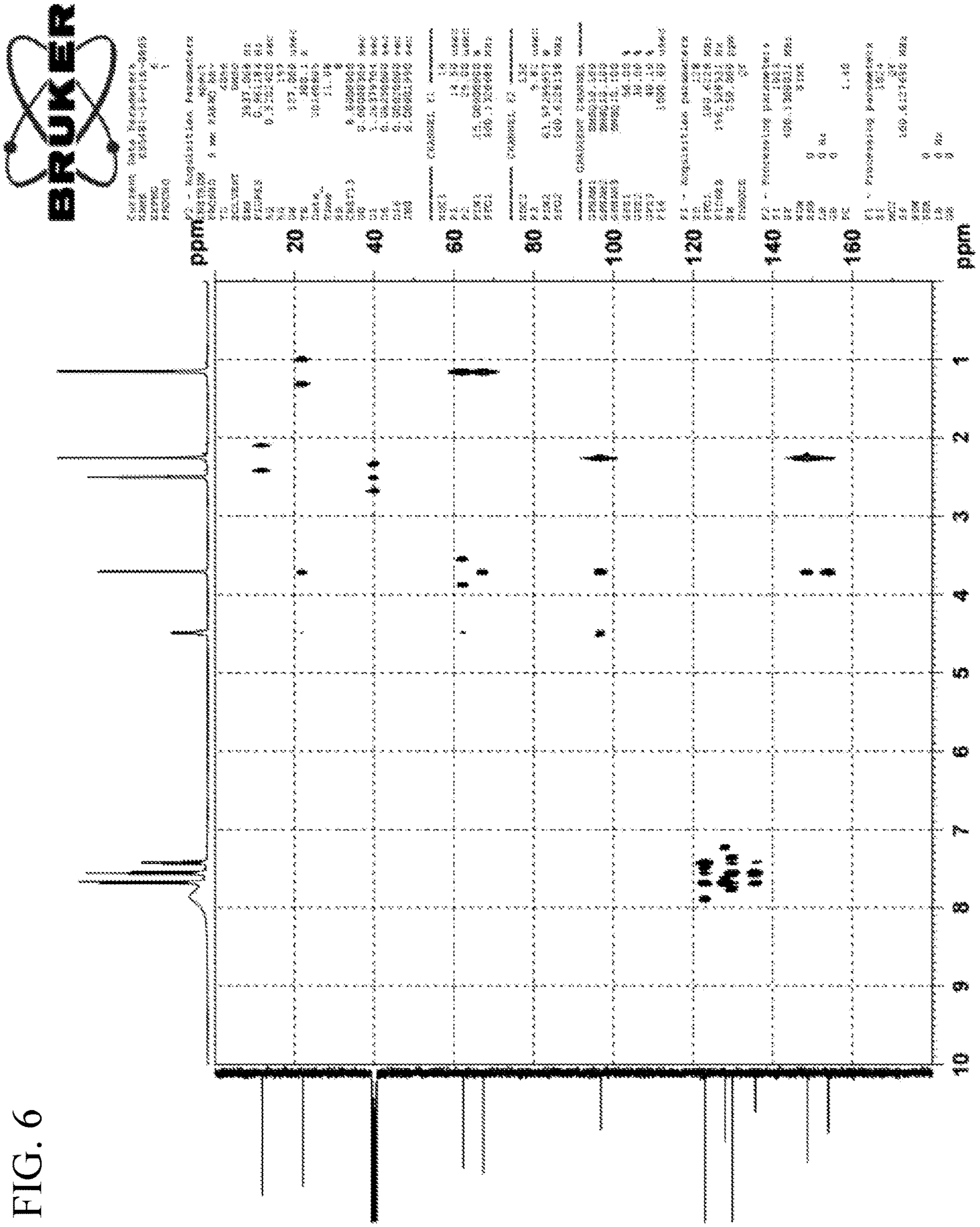
FIG. 6 is the HMBC spectrum of SCR-757.

In addition, the COSY spectrum, HSQC spectrum, and HMBC spectrum of SCR-756 and SCR-757 are as shown in FIG. 1 to FIG. 6, respectively.

The results show that SCR-756 has the structure as shown in formula I, and SCR-757 has the structure as shown in formula II.

The embodiments of the present invention are illustrated as above. However, the present invention is not limited to the above-mentioned embodiments. Any modifications, equivalent substitutions, improvements, etc. made within the spirit and principles of the present invention shall be included within the scope of protection of the present invention.

The invention claimed is:

1. A pharmaceutical composition, comprising: an active ingredient, 0.95-1.05 mg/ml of sodium metabisulfite, propylene glycol, and water for injection, wherein the active ingredient consists of 1.0-3.0 mg/ml of edaravone and 0.2-1.0 mg/ml dextrocamphol having a structural formula of

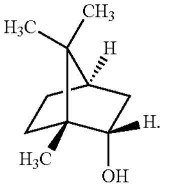

2. The pharmaceutical composition according to claim 1, wherein the weight ratio of edaravone to dextrocamphol is 1:1-4:1.

3. The pharmaceutical composition according to claim 1, comprising 2.0 mg/ml of edaravone;

and/or 0.2-1.0 mg/ml of dextrocamphol;

and/or 0.97-1.03 mg/ml of sodium metabisulphite.

4. The pharmaceutical composition according to claim 1, further comprising a compound of formula I or a pharmaceutically acceptable salt thereof, Formula I

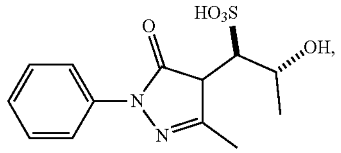

wherein the weight ratio of the compound of formula I or a pharmaceutically acceptable salt thereof to edaravone is up to 0.3%.

5. The pharmaceutical composition according to claim 1, further comprising a compound of formula II or a pharmaceutically acceptable salt thereof, Formula II

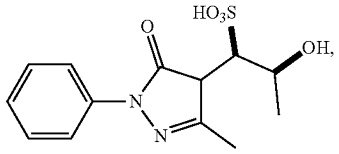

wherein the weight ratio of the compound of formula II or a pharmaceutically acceptable salt thereof to edaravone is up to 0.3%.

6. The pharmaceutical composition according to claim 4, further comprising the compound of formula II or a pharmaceutically acceptable salt thereof in a weight ratio to edaravone of up to 0.3%

Formula I

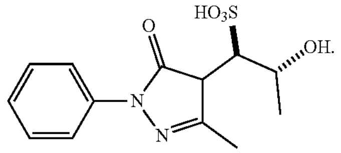

7. A method for treating cerebral stroke, comprising administering to a subject in need thereof, a therapeutically effective amount of the pharmaceutical composition according to claim 1.

8. A method for treating amyotrophic lateral sclerosis, comprising administering to a subject in need thereof, a therapeutically effective amount of the pharmaceutical composition according to claim 1.

9. The pharmaceutical composition according to claim 1, wherein the weight ratio of edaravone to dextrocamphol is 4:1.

10. The pharmaceutical composition according to claim 1, the weight ratio of edaravone, dextrocamphol and sodium metabisulphite in the pharmaceutical composition is 4:1:2.

* * * * *